(12) United States Patent
Pardridge (10) Patent No.: US 7,090,864 B2
(45) Date of Patent: Aug. 15, 2006

(54) NON-INVASIVE GENE TARGETING TO OCULAR CELLS

(75) Inventor: William M. Pardridge, Los Angeles, CA (US)

(73) Assignee: The Regents of the University of California, Los Angeles, CA (US)

( * ) Notice: Subject to any disclaimer, the term of this patent is extended or adjusted under 35 U.S.C. 154(b) by 110 days.

(21) Appl. No.: 10/025,732

(22) Filed: Dec. 19, 2001

(65) Prior Publication Data

US 2002/0054902 A1    May 9, 2002

Related U.S. Application Data

(63) Continuation-in-part of application No. 09/557,349, filed on Apr. 25, 2000, now Pat. No. 6,372,250.

(51) Int. Cl.
    *A61K 9/127* (2006.01)
(52) U.S. Cl. .................. 424/450; 424/9.1; 424/9.2
(58) Field of Classification Search .............. 424/450, 424/9.1, 9.2
    See application file for complete search history.

(56) References Cited

U.S. PATENT DOCUMENTS

| | | | |
|---|---|---|---|
| 5,154,924 A | 10/1992 | Friden | |
| 5,182,107 A | 1/1993 | Friden | |
| 5,672,683 A | 9/1997 | Friden et al. | |
| 5,833,988 A | 11/1998 | Friden | |
| 5,977,307 A | 11/1999 | Friden et al. | |
| 6,372,250 B1 * | 4/2002 | Pardridge | 424/450 |

OTHER PUBLICATIONS

Check, E. Cancer fears cast doubts on future of gene therapy. Nature 421:678, 2003.*
Verma et al. Gene therapy-promises, problems and prospects. Nature 389: 239-242, 1997.*
Monnard, P.A., Oberholzer, T., and Luisi, P. (1997) *Biochem. Biophys. Acta* 1329, 39-50.
Huwyler, J., Wu, D., and Padridge, W.M. (1996) *Proc. Natl. Acad. Sci. USA* 93, 14164-14169.
Bennett, J., Maguire, A.M., Cideciyan, A.V., et al. (1999) *Proc. Natl. Acad. Sci. USA*, 96, 9920-9925.
Lau, D., McGee, L.H., Zhou, S., Rendahl, K.G., Manning, W.C., Escobedo, J.A., and Flannery, J.G. (2000) *Invest. Ophthalmol. Vis. Sci.*, 41, 3622-3633.
Stallwood, Y., Fisher, K.D., Gallimore, P.H., and Mautner, V. (2000) *Gene Therapy*, 7, 637-643.
Smith, J.G., Raper, S.E., Wheeldon, E.B., Hackney, D., Judy, K., Wilson, J.M., and Eck, S.L. (1997) *Human Gene Therapy*, 8, 943-954.
Dewey, R.A., Morrissey, G., Cowsill, C.M., et al. (1999) *Nature Medicine*, 5, 1256-1263.
McMenamin, M.M., Byrnes, A.P., Charlton, H.M., Coffin, R.S., Latchman, D.S., and Wood, M.J.A. (1998) *Neuroscience*, 83, 1225-1237.

Herrlinger, U., Kramm, C.M., Aboody-Guterman, K.S., et al: (1998) *Gene Therapy*, 5, 809-819.
Driesse, M.J., Vincent, A.J.P.E., Sillevis Smith, P.A.E., et al, (1998) *Gene Therapy*, 5, 1122-1129.
Byrnes, A.P., Rusby, J.E., Wood, M.J.A., and Charlton, H.M. (1995) *Neuroscience*, 66, 1015-1024.
Driesse, M.J., Esandi, M.C., Kros, J.M., et al. (2000) *Gene Therapy*, 7, 1401-1409.
Kramm, C.M. Rainov, N.G., Sena-Esteves, M., Chase, M., Pechan, P.A., Chiocca, E.A., and Breakefield, X.O. (1996) *Human Gene Therapy*, 7, 291-300.
Shastry, B.S. (2000) *IUBMB Life*, 49, 479-484.
Shi, N., Zhang, Y., Boado, R.J., Zhu, C., and Pardridge, W.M. (2001) *Proc. Natl. Acad. Sci. USA*, 98, 12754-12759.
Sugasawa, K., Deguchi, J., Okami, T., Yamamoto, A., Omori, K., Uyama, M., and Tashiro, Y. (1994) *Cell. Struct. Funct.*, 19, 21-28.
Baudouin, C., Brignole, F., Fredj-Reygrobellet, D., Negre, F., Bayle, J., Gastaud, P. (1992) *Invest. Ophthalmol. Vis. Sci.*, 33, 2822-2829.
Yefimova, M.G., Jeanny, J., Guillonneau, X., Keller, N., Nguyen-Legros, J., Sergeant,C., Guillou, F., Courtois, Y. (2000) *Invest. Ophthalmol. Vis. Sci.*, 41, 2343-2351.
Brenner M., Kisseberth W.C.,.Su Y., Besnard F., Messing A. (1994) *J Neurosci.* 14, 1030-1037.
Segovia J., Vergara P., Brenner M. (1998) *Neurosci Lett.* 242, 172-176.
Kissel K., Hamm S., Schulz M., Vecchi A., Garlanda C., Engelhardt B. (1998) *Histochem Cell Biol.* 110, 63-72.
MacKenzie D., Arendt A., Hargrave P., McDowell J.H., Molday R.S. (1984) *Biochem.* 23, 6544-6549.
Shi N., Pardridge W.M. (2000) *Proc Natl Acad Sci USA* 97, 7567-7572.
Miyoshi H., Takahashi M., Gage F.H., Verma I.M. (1997) *Proc Natl Acad Sci USA.* 94, 10319-10323.
Holash J.A., Stewart P.A. (1993) *Brain Res.* 629, 218-224.
Davis A.A., Hunt R.C. (1993) *J Cell Physiol.* 156, 280-285.
Tan P.H., King W.J., Chen D., et al. (2001) *Transplantation.* 71, 552-560.
Zhuo L., Sun B., Zhang C.L., Fine A., Chiu S.Y., Messing A. (1997) *Dev Biol.* 187, 36-42.
Shi N., Boado R.J., Pardridge W.M. (2001) *Pharm Res.* 18, 1091-1095.

* cited by examiner

*Primary Examiner*—James Ketter
*Assistant Examiner*—David A. Lambertson
(74) *Attorney, Agent, or Firm*—Michael A. Gollin; Ann S. Hobbs; Venable LLP (57) ABSTRACT

Liposomes containing therapeutic genes are conjugated to multiple targeting agents to provide transport of the encapsulated gene across the blood-retinal barrier and the plasma membrane of ocular cells. Once across the blood-retinal barrier and ocular cell membrane, the encapsulated gene expresses the encoded therapeutic agent within the ocular cells to provide diagnosis and/or treatment of disease.

15 Claims, 6 Drawing Sheets
(2 of 6 Drawing Sheet(s) Filed in Color)

NON-INVASIVE GENE TARGETING TO OCULAR CELLS

This is a continuation-in-part of application Ser. No. 09/557,349 which was filed on Apr. 25, 2000 and issued as U.S. Pat. No. 6,372,250 on Apr. 16, 2001.

BACKGROUND OF THE INVENTION

1. Field of the Invention

The present invention relates generally to the delivery of gene medicines to the brain and the eye. More particularly the present invention involves the combination of liposome technology, blood-brain barrier (BBB)/blood-retinal barrier (BRB) receptor technology, pegylation technology, and therapeutic gene technology to provide formulations which are useful in the non-invasive delivery of genes to the brain and the eye.

2. Description of Related Art

The publications and other reference materials referred to herein to describe the background of the invention and to provide additional detail regarding its practice are hereby incorporated by reference. For convenience, the reference materials are numerically referenced and grouped in the appended bibliography.

The expression of exogenously administering genes in brain has previously been achieved in vivo with either viral vectors or cationic liposomes (1–4). However, in either case, highly invasive routes of administration are required. Such invasive techniques are needed because of the failure of either viruses or cationic liposomes to cross the brain capillary wall, which forms the blood-brain barrier (BBB) in vivo. The existence of the BBB necessitates the administration of the exogenous gene either intracerebrally via craniotomy (1), or by the intra-carotid arterial infusion of noxious agents that cause BBB disruption and transient opening of the BBB (4).

Human gene therapy of the brain will likely require repeated administration of the gene medicine. Therefore, it would be advantageous to administer the gene by a route that is no more invasive than a simple intravenous injection. With this approach, the gene therapeutic is delivered through the BBB by targeting the gene medicine to the brain via endogenous BBB transport systems (5). Carrier-mediated transport (CMT) systems exist for the transport of nutrients across the BBB (5). Similarly, receptor-mediated transcytosis (RMT) systems operate to transport circulating peptides across the BBB, such as insulin, transferrin, or insulin-like growth factors (5). These endogenous peptides can act as "transporting peptides," or "molecular Trojan horses," to ferry drugs across the BBB. In this approach, called the chimeric peptide technology, the drug that is normally not transported across the BBB is conjugated to a "transportable peptide, and the drug/transportable peptide conjugate undergoes RMT through the BBB (U.S. Pat. No. 4,801,575).

Peptidomimetic monoclonal antibodies (MAb) that bind endogenous transport systems within the BBB, such as the transferrin receptor (TfR) or insulin receptor, have been used in previous studies for targeting neuropeptides or antisense agents through the BBB in vivo (5). The ability of certain receptor-binding MAbs to mimic the action of the endogenous peptide that binds the same receptor is well known in the literature (31–33). In addition, the ability of such peptidomimetic MAbs, such as anti-TfR MAbs, to transport drugs into cells via these receptor-mediated endocytosis is also well known (34).

The expression in the brain of a therapeutic gene requires that the gene formulation that is injected into the blood is transported not only across the BBB by RMT, but also across the brain cell membrane (BCM) by receptor-mediated endocytosis (RME) into the target cell in brain. In addition, using endogenous BBB transport systems to target gene medicines non-invasively to the brain also requires the development of a suitable formulation of the gene therapeutic that is stable in the bloodstream. Cationic liposome/DNA complexes have been used for in vivo gene expression, but these formulations aggregate extensively in saline solution (6–11). This aggregation results in selective gene expression in the lung with little expression in peripheral tissues (12–14), and no expression in brain following intravenous administration of the cationic liposome/DNA complex (12). The DNA plasmid could be conjugated to the peptidomimetic MAb via a cationic polylysine bridge (15–17). However, electrostatic interactions between DNA and polycations may not be stable in blood, and highly polycationic proteins such as histone or polylysine exert toxic effects at the BBB and cause generalized BBB permeability changes in vivo (18).

Human blindness is a surprisingly common disorder that afflicts a large number of individuals (46). Approximately 10% of the population over 60 years of age suffers from macular degeneration, and approximately 1 in 3,000 births results in a mutation in a gene that plays an important role in vision (35). These inherited forms of blindness are collectively referred to as retinitis pigmentosa (RP). There are over 100,000 individuals in the U.S. alone that suffer from RP. The various RP genetic disorders can be traced to mutations in over 100 different genes with mutations in the rhodopsin gene comprising about 10% of RP (36).

In most cases, the mutated gene that causes RP is known, and the gene has been cloned. Therefore, gene discovery is no longer the rate-limiting issue in the gene therapy of RP. Rather, the rate-limiting problem is how to target the therapeutic gene throughout the entire retina. Present day forms of gene therapy to the retina involves packaging a therapeutic gene in a viral vector, such as adenovirus, herpes simplex virus (HSV), or adeno-associated virus (AAV). Next, the virus carrying the therapeutic gene is injected directly into each eye as either an intra-vitreal injection, or more commonly as a sub-retinal injection. The area of the retina that is tranduced with the virus is only at the tip of the injection needle. Areas of retina that are only 100 µm, which is thickness of human hair, away from the injection needle are not transduced with the exogenous gene (35).

There are at least two problems with the existing forms of gene therapy of retinal diseases. First, viral vectors are used. Virtually all humans have a preexisting immunity to either adenovirus or HSV, and the injection of these viruses into the central nervous system causes severe inflammation, which essentially aborts the therapeutic effect of the gene (36–45 and 25). More recently, AAV has been used as the viral vector because humans are less likely to have a preexisting immunity to this virus. However, single injection of AAV into the eye of a primate results in the development of high-tier neutralizing anti-AAV antibodies in the bloodstream (35). The development of these anti-viral neutralizing antibodies sets the stage for inhibiting the therapeutic effect of the subsequent gene treatments, and may also cause local inflammation within the eye.

The second problem with the existing forms of retinal gene therapy relates to the fact that the virus does not cross the blood-retinal barrier (BRB). Therefore, the virus cannot access the retina following non-invasive (intravenous, subcutaneous) forms of administration. Consequently, the viral vector carrying the exogenous gene must be administered to the retina or other structures of the eye by direct injection into the eye. This only allows for viral transduction within cells at the tip of the injection needle, which in turn would create a "pin-hole" visual field for the patient. Therefore, to have a wider distribution of the exogenous gene in the retina, it would be necessary to make multiple injections in both eyes. This would be an invasive procedure that may not be widely adapted to hundreds of thousands of patients with RP, and would also create an aberrant 'multiple pin-hole' field of vision for the patient. As is apparent, there is a present need to provide a non-viral non-invasive targeting technology for delivering therapeutic genes and other pharmaceutical agents to the entire retina.

SUMMARY OF THE INVENTION

In accordance with the present invention, therapeutic genes are introduced non-invasively into the brain across the blood brain barrier and into the eye across the blood-retinal barrier. Once inside the brain or eye, the genes express therapeutic agents which are useful in the diagnosis and treatment of brain or eye disease. The present invention is based on the use of liposomes which are capable of delivering therapeutic genes across the blood-brain barrier or the blood-retinal barrier.

The liposomes of the present invention include a neutral liposome having an exterior surface and an internal compartment in which the therapeutic gene is located. The surface of the liposome is decorated with several thousand strands of polyethyleneglycol (PEG), a process called "pegylation." The PEG strands make the surface of the liposome "hairy," and this prevents the rapid absorption of blood proteins to the surface of the liposome, which is what accelerates the rapid removal from blood of unprotected liposomes. In contrast, the pegylated liposomes are protected and are removed from blood at a much slower rate. The PEG strands also act as conjugation agents for attachment of transportable peptide targeting agents to the surface of the pegylated liposome. The transportable peptides are any kind of ligand that triggers the RMT of the complex through the BBB or BRB. In addition, the same or different transportable peptides also trigger RME through the BCM (or the plasma membrane of ocular cells) in vivo.

The therapeutic gene includes a sufficient amount of DNA to encode a therapeutic agent. A plurality of BBB/BRB targeting agents are attached to the liposome surface via a conjugation agent. The therapeutic gene located within the immunoliposome targeting vehicle is transported across the BBB/BRB and released into the interstitial space of brain or eye. Once there, the "pegylated liposome" undergoes receptor-mediated endocytosis into target cells in brain/eye because the surface of the liposome is decorated with "transportable peptides" that recognize receptor located on the brain cell or ocular cell membrane (BCM/OCM).

In many situations the same transportable targeting agent may be used to achieve transport across both the BBB/BRB and the BCM/OCM. For example, insulin or transferrin receptors are located on both the BBB/BRB and the BCM/OCM. Accordingly, the same transportable peptide targeting agent catalyzes transport across both vascular and cellular barriers. Once inside the target brain/ocular cell, the liposome complex is entrapped within brain/ocular cell endosomes, followed by release of the therapeutic gene into the cytoplasm of brain/ocular cells, where it can enter the nucleus, resulting in expression of the therapeutic agent.

It was found in accordance with the present invention that the use of liposomes in which the polyethyleneglycol is conjugated to the liposome surface results in an increase in the plasma bioavailability of the DNA incorporated within the interior of the immunoliposome. It was also found that the stability of the DNA located within the immunoliposome is increased during in vivo use. Further, in addition to achieving expression of an exogenous gene in the brain or eye, it is also possible to achieve, in parallel, gene expression in other organs which contain or express high levels of the receptor targeted by the blood-brain barrier targeting agent. The pattern of organ expression of the therapeutic gene in the body can be controlled by changing the promoter controlling the expression of the exogenous gene. The promoter is placed at the 5'-end of the therapeutic gene within the non-viral expression plasmid, that is encapsulated within the liposomes. In the present case, differential patterns of organ gene expression are obtained depending on whether a widely expressed promoter, such as the SV40 promoter, is used, or a promoter specific to neural cells is used. The neural cell specific promoter is taken from the 5'-flanking sequence of the gene for human glial fibrillary acidic protein (GFAP). When the β-galactosidase expression plasmid is driven by the SV40 promoter, this construct is called the SV40/β-galactosidase gene. Conversely, when the β-galactosidase gene is under the influence of the GFAP promoter, the plasmid is called the GFAP/β-galactosidase gene.

The above described and many other features and attendant advantages of the present invention will become better understood by reference to the following detailed description when taken in conjunction with the accompanying drawings.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

FIG. 1A is a diagrammatic representation of a preferred exemplary embodiment in which a pGL2 luciferase expression plasmid is encapsulated in an OX26 (BBB targeting agent) pegylated immunoliposomes constructed from neutral lipids. There are approximately 3000 strands of polyethylene glycol of 2000 Daltons molecular weight, designated $PEG^{2000}$, attached to the liposome surface, and about 1% of the PEG strands is conjugated with the OX26 monoclonal antibody to the rat transferrin receptor. The OX26 MAb is a peptidomimetic MAb and undergoes RMT through the BBB on the endogenous pathway that mediates BBB transport of the transferrin (5).

FIG. 1B is a graph showing that the mean diameter of the pegylated liposomes encapsulating the pGL2 plasmid DNA is 73 nm.

FIG. 1C shows electrophoresis of liposomes before (lane 2) and after (lane 1) DNAse1/exonuclease III treatment. The electrophoresis was conducted in 0.8% agarose gel electrophoresis followed by ethidium bromide (Et Br) staining. DNA molecular weight size standards are shown in the left hand side. Approximately 50% of the DNA associated with the pegylated liposome was bound to the exterior of the liposome (lane 2) and this was quantitatively removed by the nuclease treatment (lane 1). A trace amount of the pGL2 plasmid was radiolabeled with $^{32}P$ and film autoradiography of the gel showed a single 5.8 kb band with no low molecular weight radiolabeled DNA. These results show that all of the DNA is packaged in the interior of the pegylated immunoliposome.

In FIG. 1D, the conjugation of the OX26 MAb to the pegylated liposomes carrying the encapsulated pGL2 plasmid following nuclease digestion is demonstrated by Sepharose CL-4B gel filtration chromatography. A trace amount of the encapsulated pGL2 plasmid DNA was labeled with $^{32}$P and a trace amount of the OX26 MAb was radiolabeled with $^3$H. This shows the co-migration of the conjugated OX26 MAb and the encapsulated pGL2 plasmid DNA.

FIG. 5D is identical. The magnification bar in FIG. 5C is 106 µm. All specimens were counterstained with hematoxylin.

FIG. 6A shows β-galactosidase histochemistry in the eye of a control, un-injected mouse. GCL=ganglion cell layer; IPL=inner plexiform layer; INL=inner nuclear layer; OPL=outer plexiform layer; ONL=outer nuclear layer; OS=outer segments; RPE=retinal pigmented epithelium.

FIG. 6B shows β-galactosidase histochemistry of the retina obtained from a mouse injected with the SV40/β-galactosidase plasmid in accordance with the present invention showing diffuse expression in the outer retina with minimal gene expression in the inner retina or GCL.

FIG. 6C shows β-galactosidase histochemistry of an eye removed from a mouse injected with the GFAP/β-galactosidase expression plasmid in accordance with the present invention showing gene expression in the outer retina, as well as the GCL of the inner retina. There is also gene expression at the border of the IPL and the INL.

FIG. 6D shows high magnification microscopy of the outer retina after β-galactosidase histochemistry. A comparison of the distribution of rhodopsin, shown in FIG. 6H shows that the trans-gene is expressed in the RPE of the outer retina.

FIG. 6E shows expression of the trans-gene in the epithelium of the iris and ciliary body.

FIG. 6F shows expression of the trans-gene in the foamy epithelia of the sebaceous gland of the conjunctival tarsal plate.

FIG. 6H shows high magnification microscopy of the outer retina after rhodopsin immunocytochemistry.

FIG. 6G shows expression of the trans-gene in the epithelium of the corneum. All specimens shown in FIG. 6 were counterstained with hematoxylin. The magnification of FIGS. A, B, C, and E is identical, and the magnification bar in FIG. A is 37 µm. The magnification in FIGS. D, F, G, and H is identical, and the magnification bar in FIG. D is 15 µm.

DETAILED DESCRIPTION OF THE INVENTION

The immunoliposomes in accordance with the present invention are designed for delivering therapeutic genes across the blood-brain barrier followed by expression in the brain of the therapeutic agents encoded by the gene. The liposomes are a form of nanocontainer and nanocontainers, such as nanoparticles or liposomes, are commonly used for encapsulation of drugs. The liposomes preferably have diameters of less than 200 manometers. Liposomes having diameters of between 50 and 150 nanometer are preferred. Especially preferred are liposomes or other nanocontainers having external diameters of about 80 nanometers. Suitable types of liposomes are made with neutral phospholipids such as 1-palmitoyl-2-oleoyl-sn-glycerol-3-phosphocholine (POPC), diphosphatidy phosphocholine, distearoylphosphatidylethanolamine (DSPE), or cholesterol, along with a small amount (1%) of cationic lipid, such as didodecyldimethylammonium bromide (DDAB) to stabilize the anionic DNA within the liposome.

The therapeutic gene which is encapsulated within the liposome can be any of the common therapeutic genes which are used to express therapeutic and diagnostic agents. Exemplary therapeutic genes include brain-derived neurotrophic factor (BDNF) for treatment of neurodegenerative disease, stroke, or brain trauma; tyrosine hydroxylase and/or aromatic amino acid decarboxylase for Parkinson's disease; β-glucuronidase; hexosaminidase A; herpes simplex virus thymidine kinase or genes encoding antisense RNA to the epidermal growth factor receptor for treatment of brain tumors; lysosomal storage disorder replacement enzymes for Tay-Sachs and other lysosomal storage disorders; gene encoding antisense RNA for the treatment of the cerebral component of acquired immune deficiency syndrome (AIDS). Eye-specific therapeutic genes include opsin protein of rhodopsin (RHO), cyclic GMP phosophodiesterase α-subunit (PDE6A) or β-subunit (PDE6B), the alpha subunit of the rod cyclic nucleotide gated channel (CNGA1), retinal pigmented epithelium-specific 65 kD protein gene (RPE65), retinal binding protein 1 gene (RLBP1), ATP binding casette retina gene (ABCR), peripherin/retinal degeneration slow gene, rod outer segment membrane protein 1 gene (ROM1), and arrestin (SAG), which are all known to be mutated in RP. In addition, other genes are mutated in RP-related disorders, including alpha-transducin (GNAT1), rhodopsin kinase (RHOK), guanylate cyclase activator 1A (GUCA1A), retina specific guanylate cyclase (GUCY2D), the alpha subunit of the cone cyclic nucleotide gated cation channel (CNGA3), and cone opsin genes such as blue cone protein gene (BCP), green cone protein gene (GCP), and red cone protein gene (RCP), which are mutated in certain forms of color blindness.

In addition to the therapeutic gene, the plasmid DNA may also contain DNA sequences either before or after the therapeutic sequence and these additional parts of the plasmid may promote tissue-specific transcription of the plasmid in a particular cell in the brain or eye, may promote enhanced translation and/or stabilization of the mRNA of the therapeutic gene, and may enable episomal replication of the transgene in brain/eye cells. In general, the therapeutic gene will contain at least 100 nucleotides or have a molecular weight above 30,000 Daltons. It is preferred that the therapeutic gene be contained within a plasmid or other suitable carrier for encapsulation within the internal compartment of the liposome or nanocontainer.

The therapeutic gene may be encapsulated within the liposome according to any of the well known drug encapsulation processes. For example, encapsulation by sonication, freeze/thaw, evaporation, and extrusion through membrane filters.

The number of therapeutic genes encapsulated within the liposome may vary from 1 to many, depending on the disease being treated. The limiting factor will be the diameter of therapeutic gene that is encapsulated within the liposome. Using polycationic proteins such as histone, protamine, or polylysine, it is possible to compact the size of plasmid DNA that contains several thousand nucleotides to a structure that has a diameter of 10–30 nm. The volume of a 100 diameter liposome is 1000-fold and 35-fold greater than the volume of a 10 nm and 30 nm DNA compacted sphere, respectively. Therefore, it is possible to encapsulate many copies of the same gene or multiple copies of multiple genes within the liposome.

In order to provide transport of the encapsulated therapeutic gene across the BBB or BRB, a number of BBB or BRB transportable peptide targeting agents are conjugated to the surface of the liposome. Suitable targeting agents include insulin, transferrin, insulin-like growth factor, or leptin, as these peptides all have endogenous RMT systems within the BBB/BRB that also exist on the BCM/OCM. Alternatively, the surface of the liposome could be conjugated with two different transportable peptides targeting agents, one peptide targeting an endogenous BBB/BRB receptor and the other targeting an endogenous BCM/OCM peptide. The latter could be specific for particular cells within the brain, such as neurons, glial cells, pericytes, smooth muscle cells, or microglia. Specific targetable cells within the eye include cells located in the ganglion cell layer (GCL), the inner plexiform layer inner (IPL), the inner nuclear layer (INL), the outer plexiform layer (OPL), outer nuclear layer (ONL), outer segments (OS) of rods and cones, the retinal pigmented epithelium (RPE), the inner segments (IS) of rods and cones, the epithelium of the conjunctiva, the iris, the ciliary body, the corneum, and epithelium of ocular sebaceous glands. Targeting peptides may be endogenous peptide ligands of the receptors, analogues of the endogenous ligand, or peptidomimetic MAbs that bind the same receptor as the endogenous ligand. Specific targetable cells within the eye include cells located in the ganglion cell layer (GCL), the inner plexiform layer inner (IPL), the inner nuclear layer (INL), the outer plexiform layer (OPL), outer nuclear layer (ONL), outer segments (OS) of rods and cones, the retinal pigmented epithelium (RPE), the inner segments (IS) of rods and cones, the epithelium of the conjunctiva, the iris, the ciliary body, and the corneum, and epithelium of ocular sebaceous glands. The use of insulin or transferrin as transportable ligands, or the use of receptor-specific peptidomimetic monoclonal antibodies as BBB "transportable peptides" are described in detail in U.S. Pat. Nos. 4,801,575; 5,154,924; 5,182,107; 5,527,527; 5,672,683; 5,833,988; and 5,977,307. The use of an MAb to the human insulin receptor (HIR) as a BBB "transportable peptide" has been described (29).

The conjugation agents which are used to attach the BBB/BRB targeting agents to the surface of the liposome can be any of the well-known polymeric conjugation agents such as sphingomyelin, polyethylene glycol (PEG) or other organic polymers. PEG is an especially preferred conjugation agent. The molecular weight of the conjugation agent is preferably between 1000 and 50,000 DA. A particularly preferred conjugation agent is a bifunctional 2000 DA PEG which contains a lipid at one end and a maleimide group at the other end. The lipid end of the PEG binds to the surface of the liposome with the maleimide group bonding to the receptor-specific monoclonal antibody or other blood-brain barrier targeting vehicle. It is preferred that from 5 to 1000 targeting vehicles be conjugated to each liposome. Liposomes having approximately 25–40 targeting vehicles conjugated thereto are particularly preferred.

Exemplary combinations of liposomes, conjugation agents and targeting agents are as follows:

A transportable peptide such as insulin or an HIRMAb is thiolated and conjugated to a maleimide group on the tip of a small fraction of the PEG strands; or, surface carboxyl groups on a transportable peptide such as transferrin or a TfRMAb are conjugated to a hydrazide (Hz) moiety on the tip of the PEG strand with a carboxyl activator group such as N-methyl-N'-3(dimethylaminopropyl)carbodiimide hydrochloride (EDAC); a transportable peptide is thiolated and conjugated via a disulfide linker to the liposome that has been reacted with N-succinimidyl 3-(2-pyridylthio)propionate (SPDP); or a transportable peptide is conjugated to the surface of the liposome with avidin-biotin technology, e.g., the transportable peptide is mono-biotinylated and is bound to avidin or streptavidin (SA), which is attached to the surface of the PEG strand.

Figure 4:
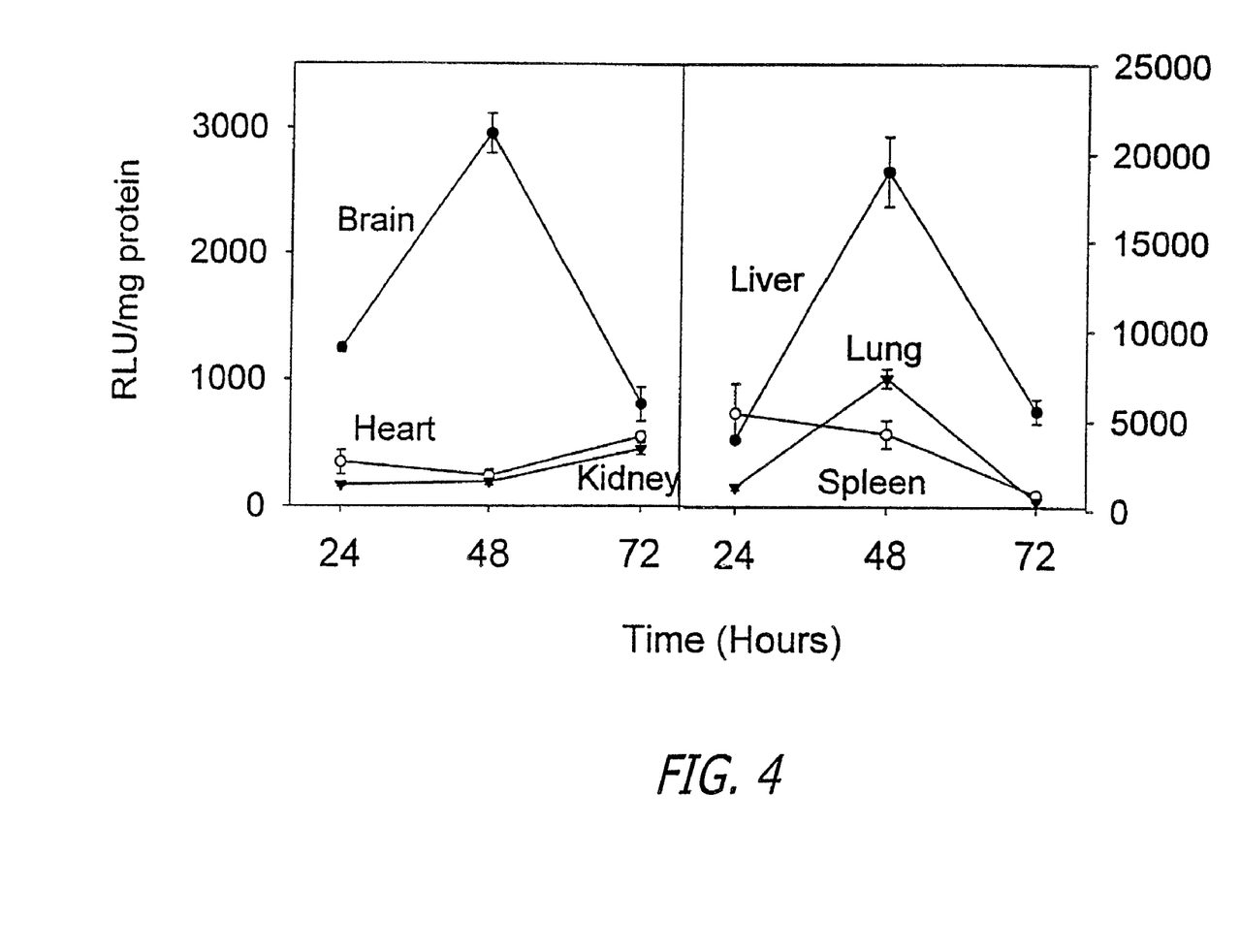
FIG. 4 depicts graphs showing the organ luciferase activity, expressed as relative light units (RLU) per mg tissue protein, for brain, heart, kidney, liver, lung, and spleen at 24, 48, and 72 hours after injection of the pGL2 plasmid DNA encapsulated in pegylated immunoliposomes that are conjugated with the OX26 MAb in accordance with the present invention. Data are mean±SE (n=3 rats/group).

Although the invention has been described using liposomes as the preferred nanocontainer, it will be recognized by those skilled in the art that other nanocontainers may be used. For example, the liposome can be replaced with a nanoparticle or any other molecular nanocontainer with a diameter <200 nm that can encapsulate the DNA and protect the nucleic acid from nucleases while the formulation is still in the blood or in transit from the blood to the intracellular compartment of the target cell. Also, the PEG strands can be replaced with multiple other polymeric substances such as sphingomylein, which are attached to the surface of the liposome or nanocontainer and serve the dual purpose of providing a scaffold for conjugation of the targeting agent and for delaying the removal of the formulation from blood and optimizing the plasma pharmacokinetics. Further, the present invention contemplates delivery of genes to any group of cells or organs which have specific target receptors. As shown in FIG. 4, the present application may be used to deliver genes to organs other than the brain or eye, such as liver, lung and spleen.

The immunoliposomes in accordance with the present invention may be combined with any suitable pharmaceutical carrier for intravenous administration. Intravenous administration of the immunoliposome is the preferred route since it is the least invasive. Other routes of administration are possible, if desired. Suitable pharmaceutically acceptable carriers include saline, Tris buffer, phosphate buffer, or any other aqueous solution.

A therapeutically effective amount of the immunoliposome will vary widely depending upon the individual being treated and the particular gene being administered. The appropriate dose will be established by procedures well known to those of ordinary skill in the art.

EXAMPLES OF PRACTICE

The following examples of the present invention describe an exogenous plasmid DNA, wherein either a β-galactosidase or a luciferase expression plasmid, driven by the SV40 promoter, is incorporated in the interior of neutral liposomes that are pegylated with PEG of 2000 Daltons molecular weight, designated PEG$^{2000}$. Approximately 40 of the PEG strands per liposome are tethered with the OX26 murine MAb to the rat transferrin receptor. The OX26 MAb, or transferrin, undergo receptor-mediated transcytosis through the BBB in vivo. The property of a peptidomimetic MAb, such as OX26, enables brain targeting of the pegylated immunoliposomes by triggering transport into brain via the BBB TfR.

Materials. POPC (1-palmitoyl-2-oleoyl-sn-glycerol-3-phosphocholine) and DDAB (didodecyldimethylammonium bromide) were purchased from Avanti Polar Lipids Inc. (Alabaster, Ala.). DSPE (distearoylphosphatidylethanolamine)-PEG$^{2000}$-maleimide was custom-synthesized by Shearwater Polymers. [α-$^{32}$P]dCTP (800 Ci/mmol) was from NEN Research Products (Boston, Mass.). $^{125}$NaI and N-succinimidyl[2,3-$^3$]propionate ($^3$H-NSP) as from Amersham LIFE SCIENCE (Arlington Height, Ill.). The nick translation system was purchased from GIBCO BRL (Fredrick, Md.). Pancreatic Dnase I (from bovine pancreases), with a specific activity of 2000 Kunitz units/mg was purchased from Sigma Chemicals (St. Louis, Mo.). Luciferase reagent, recombinant luciferase, the 6.8 kb pSV-β-galactosidase plasmid, and exonuclease III were obtained from Promega (Madison, Wis.). Protein G Sepharose CL-4B was from Pharmacia Biotech Inc. (Piscataway, N.J.). Mouse myeloma ascites IgG2a (κ) was from Cappel (Westchester, Calif.). Centriprep-30 (molecular weight cutoff: 30,000) concentrator was obtained from Amicon (Beverly, Mass.). Male Sprague Dawley rats (weighing from 200–250 g) were obtained from Harlan (Indianapolis, Ind.).

Plasmid Production. The 5.8 kb plasmid, pGL$_2$, encoding for the firefly *Photinus pyralis* luciferase gene, or the 6.8 kb pSV-β-galactosidase plasmid, both under the influence of the SV40 promoter, were obtained from Promega. The plasmids were amplified in the JM109 strain of *Escherichia coli*. DNA was extracted using alkaline lysis method and purified by precipitation with isopropanol, using Q1Afilter Plasmid Maxi kit (QIAGEN, Valencia, Calif.). DNA was measured by UV absorption at 260 nm and dissolved in TE buffer. Linearized DNA was obtained by digestion with BamHI. Its size was confirmed by 0.8% agarose gel electrophoresis and ethidium bromide staining.

DNA radiolabeling. Supercoiled DNA was labeled with [α-$^{32}$P]dCTP by the nick translation method (Nick Translation System, Promega), using DNA polymerase I and Dnase I. Unincorporated nucleotide was removed by a G25 Sephadex column (Boehringer Mannheim, IN). The specific activity of the labeled probe is 5×10$^6$ cpm/µg.

The linearized plasmid was $^{32}$P-radiolabeled at both 5' and 3' ends with T4 polymerase and purified with a Sephadex G-25 spin column to a trichloroacetic acid (TCA) precipitability of 98%. This material was analyzed with 0.8% agarose gel electrophoresis and film autoradiography and migrated as a single band of 5.8 kb with no low molecular weight radiolabeled impurities.

The $^{32}$P-linearized plasmid was used in the pharmacokinetic experiments. The $^{32}$P-supercoil plasmid was used as a tracer to measure the incorporation of the unlabeled supercoil plasmid in the liposomes.

Pegylated Liposome synthesis and plasmid DNA encapsulation. POPC (19.2 µmol), DDAB (0.2 µmol), DSPE-PEG$^{2000}$ (0.6 µmol), and DSPE-PEG$^{2000}$-maleimide (30 nmol) were dissolved in chloroform/methanol (2:1, vol:vol) followed by evaporation. The lipids were dispersed in 1 ml 0.05 M Tris-Cl buffer (pH=8.0) and sonicated for 10 minutes (20). Supercoiled DNA (100 µg) and 1 µCi $^{32}$P-DNA were added to the lipids. The liposomes/DNA dispersion was evaporated to a final concentration of 200 mM at a volume of 100 µl. The dispersion was frozen in ethanol/dry ice for 4–5 minutes and thawed at 40° C. for 1–2 minutes, and this freeze-thaw cycle was repeated 10 times. The liposome dispersion was diluted to a lipid concentration of 40 mM followed by extrusion 10 times each through 2 stacks each of 400 nm, 200 nm, 100 nm, and 50 nm pore size polycarbonate membranes, using a hand held extruder (Avestin, Ottawa, Canada), as described previously (19). The mean vesicle diameters were determined by quasielastic light scattering using a Microtrac Ultrafine Particle Analyzer (Leeds-Northrup, St. Petersburg, Fla.), as described previously (19).

The plasmid absorbed to the exterior of the liposomes was removed by nuclease digestion (20). For digestion of the unencapsulated DNA, 5 U of pancreatic endonuclease I and 5 U of exonuclease III were added in 5 mM MgCl$_2$ and 0.1 mM of DTT to the liposome/DNA mixture after extrusion. After incubation at 37° C. for 1 hour, the reaction was stopped by adding 7 mM EDTA. The extent to which the nuclease digestion removed the exteriorized plasmid DNA was determined by agarose gel electrophoresis and ethidium bromide staining of aliquots taken before and after nuclease treatment.

Conjugation of OX26 MAb or mouse IgG2a to the pegylated liposome/DNA. The anti-rat transferrin receptor OX26 mAb was harvested from serum free OX26 hybridoma conditioned media as described (21). OX26 as well as the isotype control, mouse IgG2a, were purified by protein G Sepharose affinity chromatography (21). OX26 was radiolabeled with ³H-NSP as described previously (22). The ³H-OX26 had a specific activity of 0.13 µCi/µg and a TCA precipitability of 95%.

The OX26 or mouse IgG2a (1.5 mg, 10 nmol) was thiolated using a 40:1 molar excess of 2-iminothiolane (Traut's reagent), as described previously (19). The number of OX26 molecules conjugated per liposome was calculated from the total OX26 cpm in the liposome pool and the specific activity of the labeled OX26 MAb, assuming 100,000 lipid molecules per liposome, as described previously (19). The final % entrapment of the 100 µg pGL2 in the liposome preparation was computed from the ³²P radioactivity, and was typically 30% or 30 µg plasmid DNA. This was then administered to 3 rats at a dose of 10 µg plasmid DNA per rat for luciferase gene expression measurements.

Pharmacokinetics. A pharmacokinetic study was performed in ketamine/xylazine anesthetized male Sprague Dawley rats, as described previously (19). The $^{32}$P-pGL2 (1 µCi) was injected in one of the following 3 formulations: (a) naked DNA, (b) DNA encapsulated in pegylated liposomes without antibody attached, or (c) DNA encapsulated in pegylated liposomes with OX26 MAb conjugated to the PEG strands.

Luciferase gene expression in vivo. The pegylated liposome/luciferase DNA, that was conjugated with either OX26 MAb or mouse IgG2a, was injected intravenously in anesthetized rats at a dose of 10 µg pGL2 DNA per rat. Rats were sacrificed at 24, 48 or 72 hours after injection. The brain, heart, kidney, spleen, liver and lung tissues were homogenized in 4 volumes of lysis buffer containing 0.1 M potassium phosphate buffer, pH 7.8, 1% Triton X-100, 1 mM dithiothreitol and 2 mM EDTA using a Polytron homogenizer. The homogenate was centrifuged at 14,000 rpm for 10 minutes at 4° C. The supernatant was used for measurement of tissue luciferase activity with a Luminometer (Biolumat LB 9507, Berthold, Nashua, N.H.); 100 µl of reconstituted luciferase substrate was added to 20 µl of tissue extract. Peak light emission was measured for 10 seconds at 20° C., and recorded as relative light units (RLU), as described previously (23). The background level was determined by measuring a sample containing only lysis buffer. The protein concentration in the tissue extract was determined with the bicinchoninic acid (BCA) protein assay reagent (Pierce, Rockford, Ill.).

β-Galactoside gene expression in vivo. The pegylated immunoliposome/β-galactosidase DNA was prepared exactly as described above with the OX26 MAb, and injected intravenously in rats as described above at a dose of 50 µg plasmid DNA per 0.25 kg adult rat. At 48 hours later, the brain and liver were removed, and rapidly frozen in powdered dry ice, dipped in Tissue-Tek OCT embedding medium, and 15 micron frozen sections were prepared on a Bright cryostat. The sections were fixed for 5 min at room temperature in 0.5% glutaraldehyde in 0.1 M $NaH_2PO_4$, and stored at −70 degrees, until β-galactosidase histochemistry with 5-bromo4-chloro-3-indoyl-β-D-galactose (X-gal, Promega), as described by the manufacturer. Slides were developed overnight at 37° C., and some slides were counter-stained with Mayer's hematoxylin. The slides were photographed or scanned with a 1200 dpi UMAX flatbed scanner with transilluminator, and cropped with Adobe Photoshop 5.5 with a G4 Power Macintosh.

RESULTS

Figure 1:
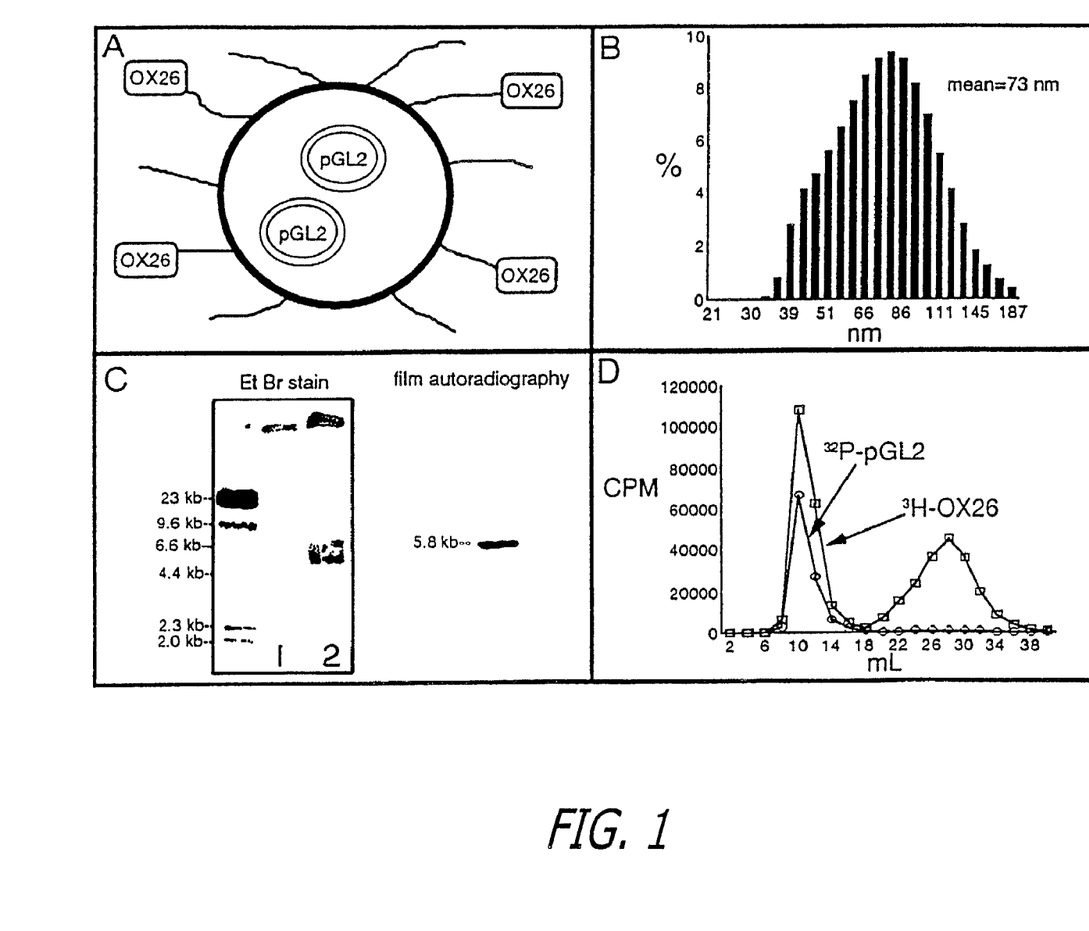

The structure of the pegylated immunoliposome carrying the pGL2 luciferase plasmid within the interior of the liposome is shown in FIG. 1A. The liposomes are formed in aqueous solution, as the mean diameter of the pegylated immunoliposomes carrying the pGL2 plasmid in the interior is 73 nm (FIG. 1b). During the formulation of the pegylated imnunoliposome carrying the plasmid DNA, the complex is treated with a mixture of nucleases (Methods). This nuclease treatment removes any plasmid DNA bound to the exterior of the pegylated liposome; ethidium bromide staining following agarose gel electrophoresis demonstrates complete removal of any exterior bound plasmid from the preparation (FIGS. 1C, lane 1). When the pGL2 plasmid DNA was radiolabeled with $^{32}$P prior to incorporation into the liposomes, only the 5.8 kb pGL2 plasmid was detected, and no low molecular weight forms of DNA were observed (FIG. 1C, film autoradiography). The covalent conjugation of the OX26 MAb to the tips of the PEG strands on the pegylated immunoliposome was monitored by Sepharose CL-4B gel filtration chromatography (FIG. 1D). These studies show co-migration of the $^{32}$P-pGL2 incorporated in the interior of the liposome with the ³H-labeled OX26 MAb attached to the PEG strands. Based on the specific activity of the OX26, it was calculated that this preparation of pegylated immunoliposome contained 39 molecules of OX26 MAb conjugated to the individual liposome.

Figure 2:
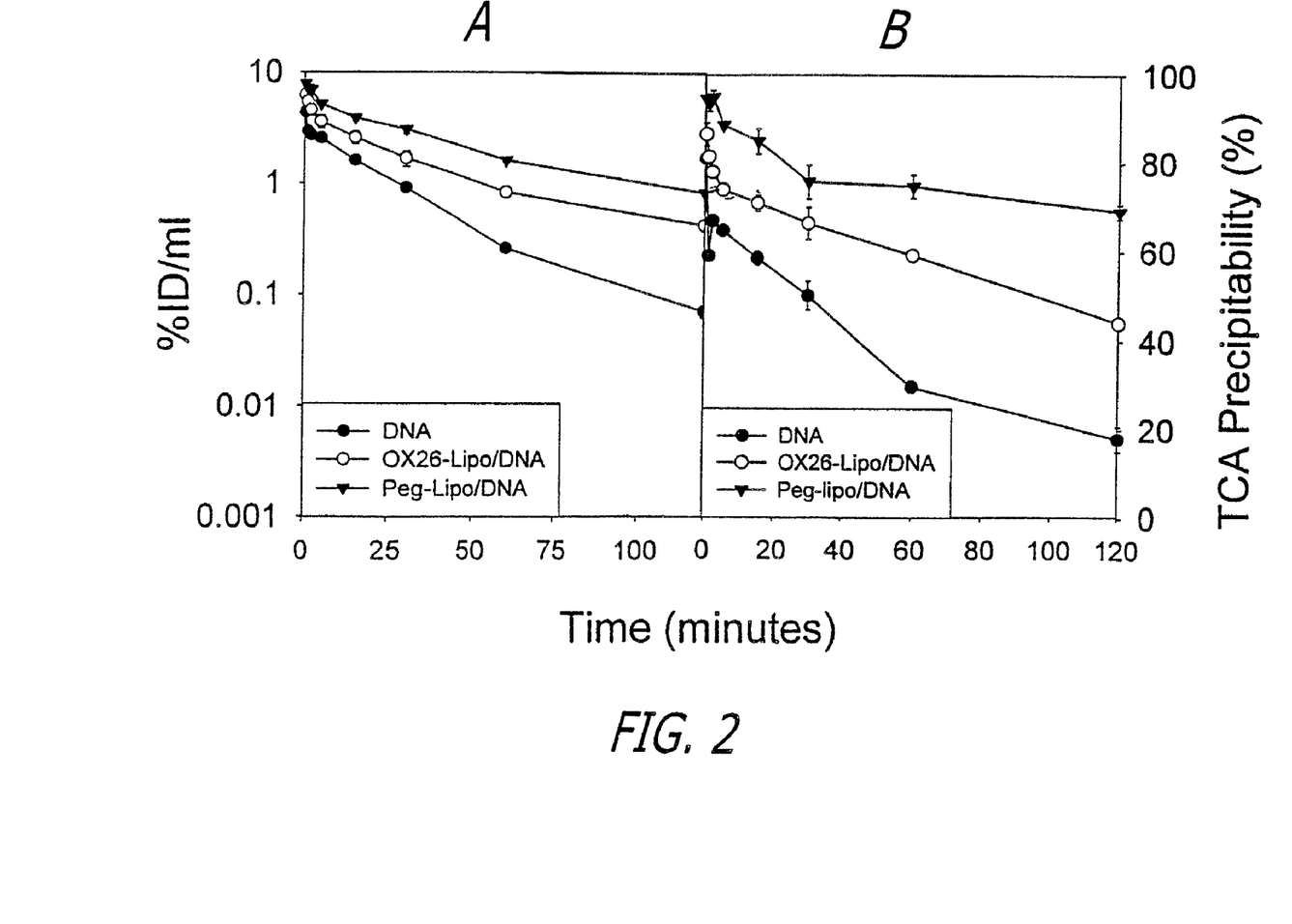
FIG. 2A shows a graph in which the percent of injected dose (ID) per mL plasma that is precipitated by trichloroacetic acid (TCA) is plotted versus the time after intravenous injection of the $^{32}$P DNA in anesthetized rats for up to 120 minutes. The DNA was injected 1 of 3 formulations: (a) "naked" DNA (DNA), (b) pGL2 plasmid DNA encapsulated within the interior of nuclease treated OX26 pegylated immunoliposomes (OX26-Lipo/DNA), and (c) pGL2 plasmid DNA encapsulated in the interior of nuclease treated pegylated liposomes without OX26 MAb attached (Peg-Lipo/DNA).
FIG. 2B is a graph showing the percent of plasma radioactivity that is precipitated by TCA. Data mean are ±SE (n=3 rats/group).
Figure 3:
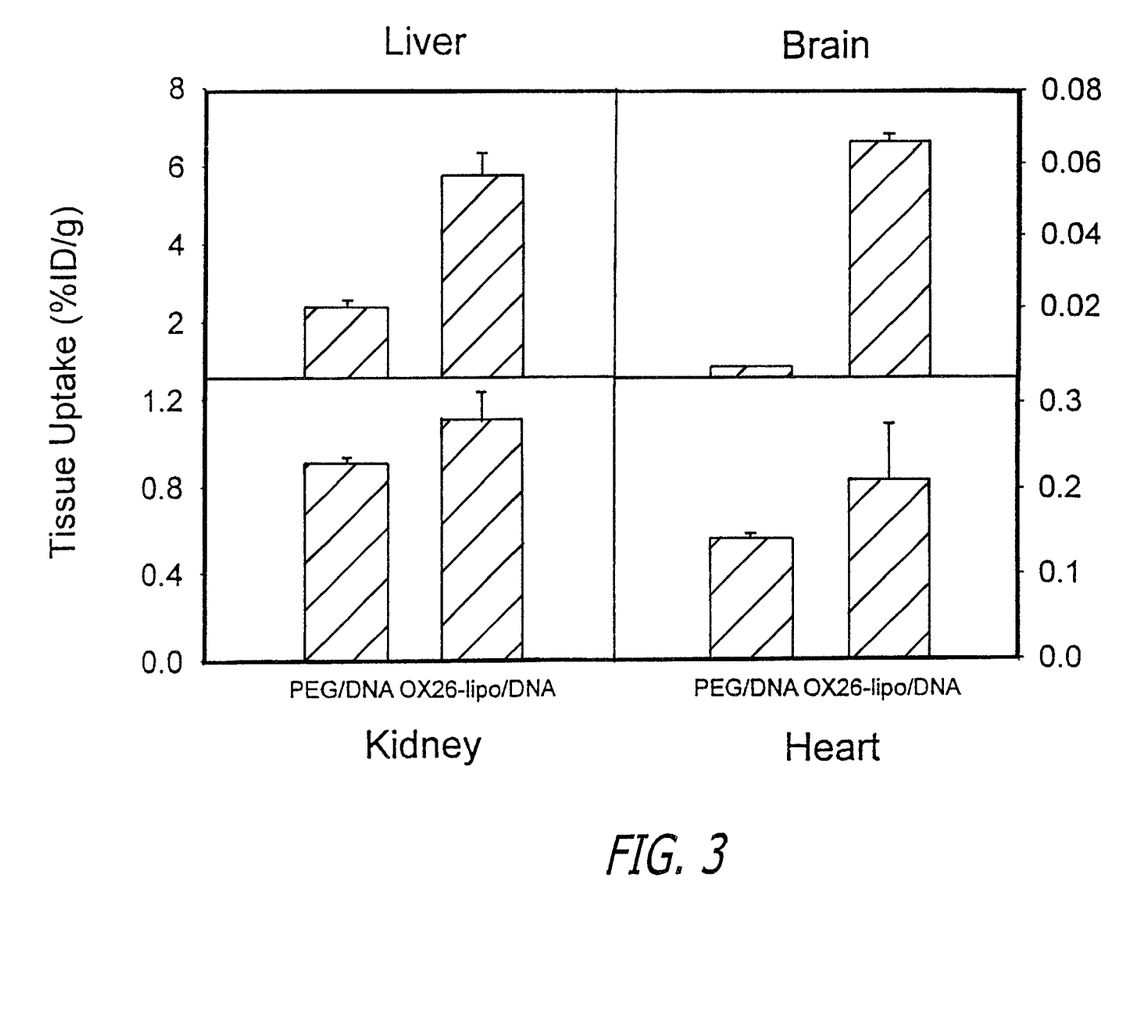
FIG. 3 depicts graphs in which the tissue uptake, expressed as % injected dose (ID) per gram tissue for liver, brain, kidney, or heart is shown at 120 minutes after intravenous injection of the encapsulated $^{32}$PGL2 plasmid DNA incorporated in either pegylated liposomes without antibody attached (PEG/DNA) or within the OX26 pegylated immunoliposomes (OX26-Lipo/DNA). Data are mean±SE (n=3 rats/group).

The pharmacokinetic studies were performed with the linearized pGL2 plasmid DNA, which was end labeled with $^{32}$P. This was then injected into anesthetized rats in 1 of 3 forms: (a) naked DNA, (b) $^{32}$P-pGL2 plasmid incorporated in the interior of pegylated liposomes conjugated with no MAb, and (c) $^{32}$P-pGL2 plasmid DNA incorporated into the interior of pegylated immunoliposomes conjugated with OX26. These 3 different preparations were each injected into different groups of rats and the plasma radioactivity that was precipitated with trichlororacetic acid (TCA) was determined at various times up to 2 hours after intravenous administration (FIG. 2, right panel). The naked DNA was rapidly removed from the plasma with a clearance (Cl) of 4.1±0.5 mL/min/kg and a systemic volume of distribution (Vss) of 514±243 mL/kg. The Cl of the DNA was reduced more than 4-fold to 0.95±0.05 mL/min/kg when the DNA was incorporated in the interior of pegylated liposomes carrying no OX26 MAb (FIG. 2, left panel). The systemic clearance increased to 2.3±0.2 mL/min/kg when the OX26 MAb was tethered to the tip of the PEG tail of the liposome. The tissue uptake in brain, liver, kidney, and heart was also measured. These data show that attachment of the OX26 MAb to the tip of the pegylated liposome carrying the DNA exerted minor increases in tissue uptake in kidney or heart, moderate increases in liver, and a marked increase in the brain uptake of the pegylated immunoliposome (FIG. 3). The pegylated liposome carrying the plasmid DNA that had no OX26 tethered to the PEG strand was not significantly taken up by brain (FIG. 3). However, the OX26 pegylated liposome carrying the plasmid DNA was taken up by brain at a level of 0.066±0.002% ID/g brain at 120 minutes after intravenous injection (FIG. 3). This level of brain uptake is comparable to that of a neuroactive small molecule such as morphine, which has a brain uptake of 0.081±0.001% ID/g brain at 60 minutes after injection in the anesthetized rat (24).

The luciferase gene expression in brain and peripheral tissues was examined in a group of rats administered 10 µg of plasmid DNA per rat, which was incorporated in the interior of OX26 pegylated immunoliposomes. Organ luciferase enzyme activity, expressed as relative light units (RLU) per mg tissue protein, was measured at 24, 48, and 72 hours after intravenous injection. Although there was minimal targeting of the luciferous gene in the heart or kidney, the luciferase gene expression in brain was comparable to that of lung or spleen and peaked at 48 hours after intravenous administration (FIG. 4). The peak luciferase gene expression in liver was approximately 6-fold higher in that organ relative to brain, owing to the abundant expression of transferrin receptor on hepatocyte plasma membranes. For control studies, pegylated immunoliposomes were prepared except mouse $IgG_{2a}$, which is the same isotype as OX26, was conjugated to the pegylated liposomes in lieu of the OX26 MAb. The mouse $IgG_{2a}$ pegylated immunoliposome/pGL2 DNA complex was intravenously injected in anesthetized rats; the dose of pGL2 plasmid DNA was 10 μg per rat, or 40 μg per kg. However, there was no measurable luciferase expression in brain or in any of the other organs at 48 hours after intravenous administration. This control experiment was repeated 3 times, and the luciferase activity was below the limits of detection in all samples.

The above examples of practice demonstrate in accordance with the present invention that it is possible to achieve widespread expression of an exogenous gene in the brain following non-invasive intravenous administration. Replacement of the SV40 promoter and 3-untranslated region (UTR) parts of the plasmid with tissue- and gene-specific promoters and 3-UTR elements should enable region- and even cell-specific gene expression in the brain. This approach to gene therapy is well-suited for use in humans by simply changing the MAb moiety of the formulation (FIG. 1A) to the human insulin receptor (HIR) MAb (29) which is nearly 10 times more active in primates than is the anti-TfRMAb (5). Chimeric forms of the HIRMAb have been recently described, and the genetically engineered chimeric HIRMAb has identical transport properties at the primate or human BBB as does the original murine antibody (30).

The following example demonstrates the expression of an exogenous gene in the eye. The exogenous gene used in this example is the same gene encoding for bacterial β-galactosidase that was used in the preceding examples. The bacterial β-galactosidase gene is placed in a non-viral expression plasmid, which is driven by either an SV40 promoter or the human GFAP promoter. The double-stranded, supercoiled plasmid is packaged in the interior of the pegylated immunoliposomes (PIL) that are targeted to the mouse eye with the rat 8D3 monoclonal antibody (MAb) to the mouse transferrin receptor (TfR). The PIL is shown diagrammatically in FIG. 5A.

The details of the formulation of the PIL and the encapsulation of the therapeutic gene in the interior of the PIL are described in the previous example. However, the previous examples were performed in rats for organs such as brain, liver, and spleen using the mouse OX26 MAb to the rat TfR. However, the OX26 MAb is not active in mice; therefore, it was necessary to develop a vector specific for mice. For gene targeting to mouse organs, we use the rat 8D3 MAb to the mouse TfR (26, 47). This 8D3 MAb acts as a targeting agent and is tethered to the tips of the polyethyleneglycol (PEG) strands on the PIL in the same manner as the previous examples.

The TfR was targeted because the TfR is expressed on both the BRB and on the plasma membranes of retinal and other ocular cells. In order for the therapeutic gene to be expressed in cells in the retina, the PIL must be transported across two barriers in vivo. The first barrier is the blood-retinal barrier, which is localized either to the retinal capillary endothelium or to the retinal pigmented epithelium (RPE). The second barrier is the plasma membrane of the retinal cells. The TfR is expressed on both of these barriers. Prior work has shown that the TfR is expressed at the BRB, ganglion cell layer, the inner nuclear layer, the outer plexiform layer, inner segments of rods and cones, the RPE, the epithelium of the conjunctiva, the epithelium of the iris, and the epithelium of the ciliary body (48–50, 57–60).

Details of the present example are set forth as follows:

Materials

Adult male BALB/c albino mice (25–30 g) were purchased from Harlan (Indianapolis, Ind.). The pSV-β-galactosidase expression plasmid under the influence of the SV40 promoter was obtained from Promega (Madison, Wis.). The β-galactosidase staining kit was purchased from Invitrogen (San Diego, Calif.). The pGfa-lacZ β-galactosidase expression plasmid was provided by Dr. Jose Segovia of the Centro de Investigacion y de Estudies Avanzados (San Pedro Zacatenco, Mexico). In this plasmid, the lacZ gene is driven by the human glial fibrillary acidic protein (GFAP) promoter, as described previously (51, 52). The 8D3 hybridoma line, secreting a rat IgG to the mouse transferrin receptor (53), was obtained from Dr. Britta Engelhardt of the Max Planck Institute (Bad Nauheim, Germany), and the 8D3 MAb was purified as described in (47). The 1D4 mouse monoclonal antibody against bovine rhodopsin (54) was obtained from Dr. Dean Bok of the UCLA School of Medicine (Los Angeles, Calif.). The Vector M.O.M. immunodetection kit, AEC substrate kit for peroxidase and hematoxylin QS counter-stain were purchased from Vector Laboratories (Burlingame, Calif.). Tissue-Tek OCT compound was purchased from Sakura FineTek (Torrance, Calif.). The mouse monoclonal antibody against porcine GFAP and all other reagents were purchased from Sigma (St. Louis, Mo.).

In vivo Administration of Pegylated Immunoliposomes

As mentioned above the 8D3 PIL carrying either the pSV-β-galactosidase (designated SV40/β-galactosidase) or the pGfa-lacZ (designated GFAP/β-galactosidase) were prepared in the same manner as the previous example. Male BALB/c mice of 25–30 g body weight were anesthetized with ketamine (50 mg/kg) and xylazine (4 mg/kg) intraperitoneally. Experimental animals (n=8) were injected intravenously through the femoral vein with 8D3 PIL carrying either pSV-β-galactosidase plasmid DNA (n=3) or the pGfa-lacZ plasmid DNA (n=5) at a dose of 5–6 μg/per mouse. Control mice (n=3) were anesthetized and sacrificed without receiving any injection.

Mice were sacrificed at 48 hours after the single intravenous injection. Eyes were removed and frozen in OCT embedding medium on dry ice and stored at −70° C. Alternatively, some mice underwent perfusion fixation with 4% paraformaldehyde in situ prior to removal of the eyes. These eyes were immersion fixed in 4% paraformaldehye, cryo-protected overnight in 30% sucrose, and then frozen in OCT medium prior to preparation of frozen sections.

Beta Galactosidase Histochemistry

Beta galactosidase histochemistry was performed on frozen sections of the eyes similar to prior work reported for brain (47, 55 and 62). Horizontal frozen sections of 18 μm thickness were cut on an HM505 microtome cryostat (Micron Instruments, San Diego, Calif.), and fixed with 0.5% glutaraldehyde in 0.01 M PBS (pH 7.4) for 5 minutes. After wash in PBS, sections were incubated in X-GAL staining solution (4 mM potassium ferricyanide, 4 mM potassium ferrocyanide, 2 mM $MgCl_2$, and 1 mg/ml X-gal, pH 7.4) at 37° C. overnight, where X-gal=5-bromo-4-chloro-3-indoyl- β-D-galactoside. After the staining, sections were briefly washed in distilled water and lightly counterstained with hematoxylin.

Immunohistochemistry

Immunohistochemistry for rhodopsin and GFAP was performed with the Vector M.O.M. immunodetection kit. Frozen sections of the eyes from the control and experimental animals were fixed in pre-cooled acetone at −20° C. for 20 minutes or in 2% paraformaldehyde for 20 minutes at 4° C. Endogenous peroxidase was blocked with 0.3% $H_2O_2$ in 0.3% horse serum for 5 minutes. Non-specific binding of proteins was blocked with Vector M.O.M mouse immunoglobulin blocking solution for 1 hour. Sections were then incubated in the primary antibody, 1D4 mouse anti-bovine rhodopsin MAb (5 μg/ml) or mouse anti-porcine GFAP MAb (8 μg/ml) for 30 minutes at room temperature. After wash in PBS, sections were incubated in M.O.M. biotinylated anti-mouse IgG for 10 minutes and then in Vectastain Elite ABC horseradish peroxidase for 5 minutes. After developing with 3-amino-9-ethylcarbazole (AEC), sections were lightly counterstained with hematoxylin and mounted with glycerol/gelatin. Whole mount images of the eye were obtained by scanning the stained section with a UMAX PowerLookIII scanner with transparency adapter, and the image was cropped in Adobe Photoshop 5.5 on a G4 Power Macintosh computer.

Figure 5:
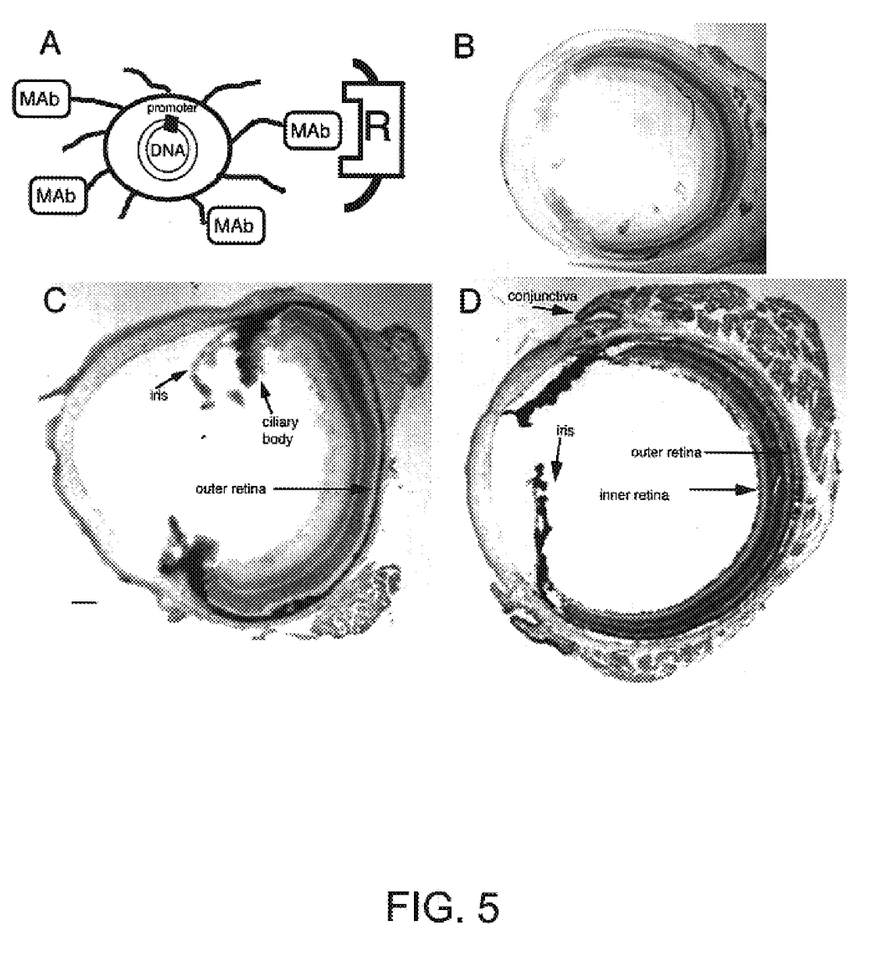
FIG. 5A is a diagrammatic representation of a receptor-specific liposome in accordance with the present invention wherein a non-viral, supercoiled, double-stranded plasmid DNA driven by a cell-specific promoter is packaged in the interior of a 75–100 nm liposome. The surface of the liposome is decorated with several thousand strands of 2000-Dalton polyethyleneglycol (PEG), and the tips of 1–2% of the PEG strands are conjugated with a receptor (R)-specific targeting monoclonal antibody (MAb). The MAb triggers the receptor-mediated transcytosis of the pegylated immunoliposome across the blood-retinal barrier, and triggers the receptor-mediated endocytosis of the receptor-specific liposome into cells of the eye expressing the targeted receptor.
FIG. 5B shows the β-galactosidase histochemistry in a control eye obtained from a mouse that was not injected with a PIL in accordance with the present invention.
FIG. 5C shows the β-galactosidase histochemistry in an eye obtained 48 hours after intravenous injection of the SV40/β-galactosidase plasmid in accordance with the present invention. There is diffuse expression of the trans-gene in the outer retina, as well as the iris and ciliary body.
FIG. 5D shows β-galactosidase histochemistry in the mouse eye obtained 48 hours after intravenous injection of the GFAP/β-galactosidase plasmid in accordance with the present invention. There is diffuse expression of the trans-gene in both the inner retina and the outer retina, as well as the iris and conjunctival epithelium. The magnification of FIG. 5C

RESULTS

β-galactosidase histochemistry was performed on mouse eye sections obtained from animals that had not been injected with any exogenous gene, and the histochemistry shows the absence of any endogenous β-galactosidase enzyme product (see FIG. 5B). The β-galactosidase histochemistry of the eye removed 48 hours after single intravenous injection of the 8D3 PIL carrying the β-galactosidase expression plasmid driven by the SV40 promoter is shown in FIG. 5C. This demonstrates diffuse expression of the exogenous gene in the outer retina, as well as gene expression in the ciliary body and iris (FIG. 5C). When the β-galactosidase expression plasmid was driven by the GFAP promoter and packaged in the interior of the 8D3 PIL, the exogenous gene was expressed in both the inner and outer retina, as shown in FIG. 1D. This section also shows gene expression in conjunctival epithelium, and in the ciliary body and the iris (FIG. 5D).

Figure 6:
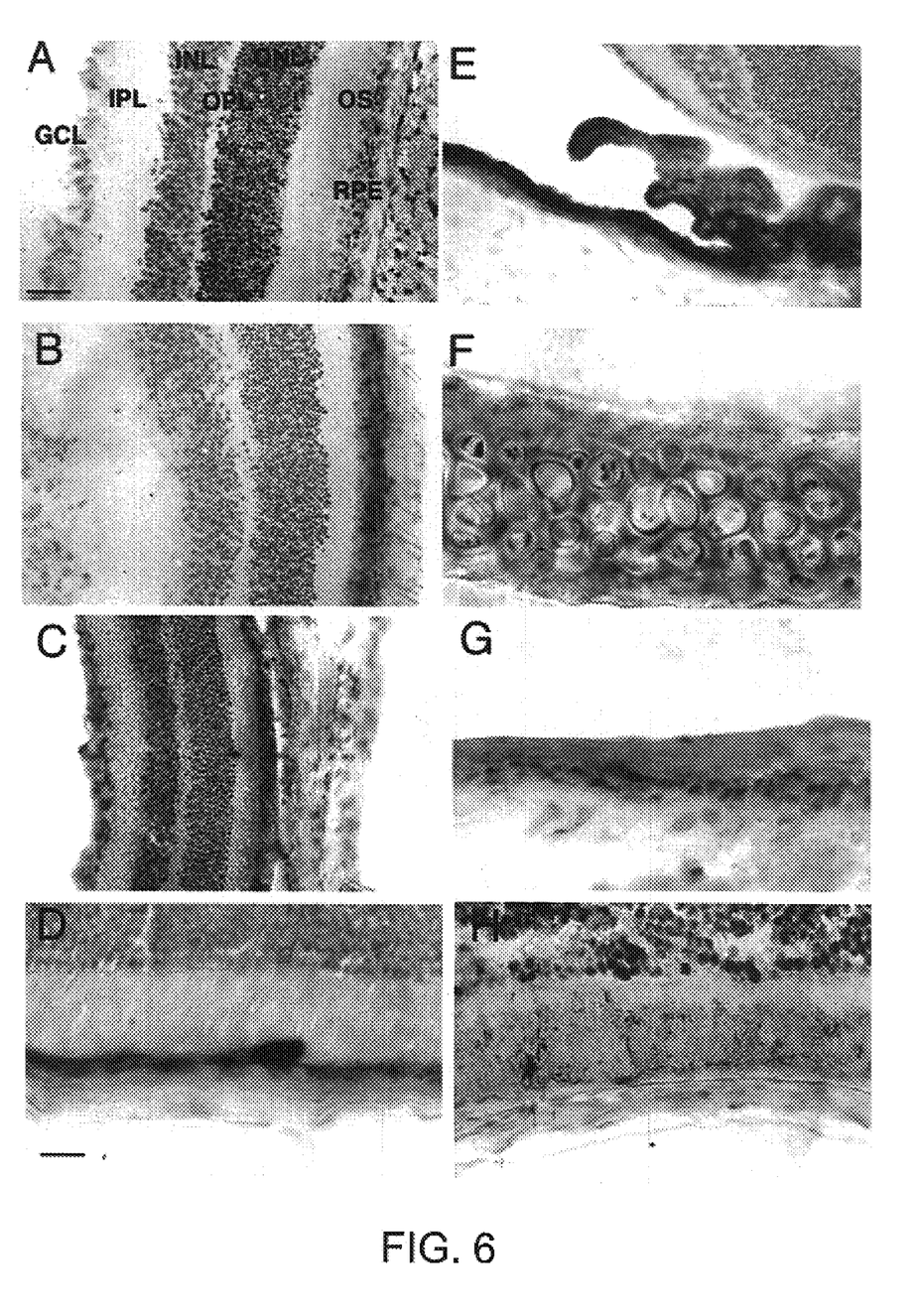

High magnification microscopy of the retina removed from control, un-injected mice shows the absence of endogenous β-galactosidase histochemical product (FIG. 6A). Following the intravenous administration of the SV40/β-galactosidase plasmid, the predominant pattern of gene expression is in the outer retina at a location corresponding to the junction of the outer segments and the retinal pigment epithelium (RPE), as shown in FIG. 6B. Gene expression in the cells of the inner retina at the GCL is demonstrated in FIG. 6C, which is β-galactosidase histochemistry of an eye removed from mice treated with the GFAP/β-galactosidase plasmid. GFAP immunocytochemistry was performed on parallel sections (data not shown), and there was overlap of the GFAP immunopositive cells in the GCL of the inner retina and the β-galactosidase histochemical product, as shown in FIG. 6C. Higher magnification views of the outer retina are shown in FIGS. 6D and 6H for the β-galactosidase histochemistry and for the rhodopsin immunocytochemistry, respectively. The outer segments (OS) and the inner segments (IS), which are immuno-positive and immuno-negative, respectively, for rhodopsin are visible in FIG. 6H. Based on comparison of the β-galactosidase histochemistry (FIG. 6D) and the rhodopsin immunocytochemistry (FIG. 6H), it appears that exogenous gene expression in the outer retina is restricted to the RPE.

The exogenous gene is also expressed in the epithelium of the ciliary body and iris (FIG. 6E). The tarsal plate sebaceous gland epithelium, with the characteristic foamy appearance, expresses the exogenous gene, as shown in FIG. 6F. The epithelium of the corneum demonstrated expression of the trans-gene, as shown in FIG. 6G.

The above example demonstrates that it is possible to target an exogenous gene throughout the entire retina and other structures of the eye following a simple intravenous injection, if gene targeting technology in accordance with the present invention is used. Second, the expression of the exogenous gene in different cell layers of the retina can be modulated with cell-specific promoters, as shown by the selective expression of the β-galactosidase gene in the GCL following administration of the expression plasmid driven by the GFAP promoter (FIG. 6C).

If a non-specific IgG molecule is conjugated to the tips of the PEG strands, in lieu of the targeting MAb (FIG. 5A), and injected intravenously in rats or mice, there is no expression of the exogenous gene in brain or other tissues (47, 55, and 62). However, the PIL can be delivered to tissues based on the tissue-specific expression of the targeted receptor (R), if a targeting MAb is conjugated to the PEG strands, as outlined in FIG. 5A. An MAb to the TfR is used to target the PIL carrying the DNA to cells in vivo. Gene expression in brain cells is possible with the PIL gene targeting in accordance with the present invention because the TfR is expressed on both the brain capillary endothelium, which forms the blood-brain barrier (BBB) (27), and on the plasma membrane of brain cells (28). Similarly, the TfR is widely expressed at the BRB in the eye (57). The TfR is also expressed on the plasma membrane of multiple cells of the eye, including cells of the GCL, the inner nuclear layer (INL), the RPE, and the IS of the photoreceptor cells (57–59). The TfR is expressed in the epithelium of the conjunctiva, the iris, the ciliary body, and the corneum (49, 60). The pattern of gene expression in the eye as shown in FIGS. 5C and 5D parallels the diffuse expression of the TfR in the eye. Owing to the dual expression of the TfR on both the BRB and the plasma membrane of ocular cells, the PIL in accordance with the present invention is able to deliver the exogenous gene across the different cellular barriers separating the blood from the intracellular compartment of cells within the eye.

Once the exogenous gene is delivered to the intracellular compartment, it is possible to influence the cellular specificity of gene expression with the use of cell-specific gene promoters. The expression of an exogenous gene can be restricted to the brain with PIL gene targeting in accordance with the present invention if a brain-specific promoter, such as the GFAP gene promoter, is inserted in the expression plasmid in lieu of the SV40 promoter (47). Under normal conditions, the only structure that expresses GFAP in the retina is the GCL (61). There is minimal expression of the β-galactosidase gene in the GCL when the plasmid is driven by the SV40 promoter (FIG. 5B). However, if the SV40 promoter is replaced with the GFAP promoter, then cells of the GCL express the β-galactosidase gene (see FIG. 6C). Accordingly, it is possible to enhance expression of an exogenous gene in cells of the ONL and photoreceptor segments, if an opsin gene promoter is inserted in the expression plasmid, as has been shown previously with viral delivery systems (56).

The above examples demonstrate that it is possible to obtain diffuse expression of an exogenous gene throughout the retina following an intravenous injection of a non-viral formulation. With the expression plasmid used in the present studies, the exogenous gene is expressed within cells as an extra-chromosomal episome, and gene expression is necessarily transient. The half-time of expression of an exogenous gene driven by the SV40 promoter and delivered with the PIL system to organs in the rat is approximately 6 days (62). Therefore, as discussed previously, the PIL would have to be administered at repeat periodic intervals based on the persistence of the trans-gene. Repeat administration of the PIL should is possible since the only immunogenic component of the formulation is the MAb, and the immunogenicity of the MAb in humans can be reduced or eliminated with genetic engineering and the production of "humanized antibodies."

The PIL gene targeting set forth in the above example can be used in humans by replacement of the anti-TfR MAb with an MAb to the human insulin receptor (HIR) (29) or other suitable targeting agent. It has been shown that genetically engineered HIRMAb readily the primate BBB in vivo and binds to the human BBB in vitro, owing to the high on of the insulin receptor at the BBB (30). Since the insulin receptor is also ed at the BRB (63), the genetically engineered HIRMAb is also expected to target PIL-encapsulated genes into the retina in humans.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

BIBLIOGRAPHY

1. Culver, K. W., Ram, Z., Wallbridge, S., Ishii, H., Oldfield, E. H., and Blaese, R. M. (1992) *Science* 256, 1550–1552.
2. Suhr, S. T. and Gage, F. H. (1993) *Arch Neurol.* 50, 1252–1268.
3. Martin, J. B. (1995) *Trends Biotechnol.* 13, 28–35.
4. Nilaver, G., Muldoon, L. L., Kroll, R. A., Pagel, M. A., Breakefield, X. O., Davidson, B. L., and Neuwelt, E. A. (1995) *Proc. Natl. Acad. Sci. USA* 92, 9829–9833.
5. Pardridge, W. M. (1997) *J. Cereb. Blood Flow. Metabol.* 17, 713–731.
6. Reimer, D. L., Zhang, Y., Kong, S., Wheeler, J. J., Graham, R. W., and Bally, M. B. (1995) *Biochem* 34, 12877–12883.
7. Matsui, H., Johnson, L. G., Randell, S. H. and Boucher, R. C. (1997) *J. Biol. Chem.* 272, 1117–1126.
8. Mahato, R. I., Rolland, A., and Tomlinson, E. (1997) *Pharm. Res.* 14, 853–859.
9. Huang, L. and Li, S. (1997) *Nature Biotech.* 15, 620–621.
10. Niidome, T., Ohmori, N., Ichinose, A., Wada, A., Mihara, H., Hirayama, T., and Aoyahi, H. (1997) *J. Biol. Chem.* 272, 15307–15312.
11. Plank, C., Tang, M. X., Wolfe, A. R., and Szoka, F. C. (1999) *Human Gene Therapy* 10, 319–332.
12. Osaka, G., Carey, K., Cuthbertson, A., Godowski, P., Patapoff, T., Ryan, A., Gadek, T., and Mordenti, J. (1996) *J. Phamr. Sci* 85, 612–618.
13. Holland, H. E. J., Nagy, D., Liu, J.-J., Spratt, K., Lee, Y. L., Danos, O., and Sullivan, S. M. (1997) *Pharm. Res.* 14, 742–749.
14. Song, Y. K., Liu, F., Chu, S., and Liu, D. (1997) *Human Gene Therapy* 8, 1585–1594.
15. Wu, G. Y. and Wu, C. H. (1987) *J. Biol. Chem.* 262, 4429–4432.
16. Chowdhury, N. R., Wu, C. H., Wu, G. Y., Yemeni, P. C., Bommineni, V. R., and Chowdhury, J. R. (1993) *J. Biol. Chem.* 268, 11265–11271.
17. Perales, J. C., Grossmann, G. A., Molas, M., Liu, G., Ferkol, T., Harpst, J., Oda, H., and Hanson, R. W. (1997) *J. Biol Chem.* 272, 7398–7407.
18. Pardridge, W. M., Triguero, D., and Buciak, J. B. (1989) *J. Pharmacol. Exp. Ther.* 251, 821–826.
19. Huwyler, J., Wu, D., and Pardridge, W. M. (1996) *Proc. Natl. Acad. Sci. USA* 93, 14164–14169.
20. Monnard, P. A., Oberholzer, T., and Luisi, P. (1997) *Biochem. Biophys. Acta* 1329, 39–50.
21. Kang, Y.-S. and Pardridge, W. M. (1994) *J. Pharmacol. Exp. Ther.* 269, 344–350.
22. Pardridge, W. M., Buciak, J. L., and Yoshikawa, T. (1992) *J. Pharmacol. Exp. Ther.* 261, 1175–1180.
23. Dwyer, K. J., Boado, R. J., and Pardridge, W. M. (1996) *J. Neurochem.* 66, 449–458.
24. Wu, D., Kang, Y.-S., Bickel, U., and Pardridge, W. M. (1997) *Drug Metab. Disp.* 25, 768–771.
25. Wood, M. J. A., Charlton, H. M., Wood, K. J., Kajiwara, K., and Byrnes, A. P. (1996) *Trends Neurosci.* 19, 497–501.
26. Lee, H. J., Engelhardt, B., Lesley, J., Bickel, U., and Pardridge, W. M. (2000) *J. Pharmacol. Exp. Ther.* 292, 1048–1052.
27. Huwyler, J. and Pardridge, W. M. (1998) *J. Neurochem.* 70, 883–886.
28. Mash, D. C., Pablo, J., Flynn, D. D., Efange, S. M. and Weinger, W. J. (1990) *J. Neurochem.* 55, 1972–1979.
29. Pardridge, W. M., Kang, Y.-S., Buciak, J. L., and Yang, J. (1995) *Pharm Res.,* 12, 807–816.
30. Coloma, M. J., Lee, H. J., Kurihara, A., Landaw, E. M., Boado, R. J., Morrison, S. L., and Pardridge, W. M. (2000) *Pharm Res.,* 17, 266–264
31. Beisiegel, U., Schneider, W. J., Goldstein, J. L., Anderson, R. G. W., and Brown, M. S. (1981) *J. Biol. Chem.* 256, 11923–11931.
32. Shechter, Y., Maron, R., Elias, D., and Cohen, I. R. (1982) *Science* 216, 542–545.
33. Soos, M. A. et al. (1989) *Proc. Natl. Acad. Sci, USA,* 86, 5217–5221.
34. Domingo, D. L. and Trowbridge, I. S. (1985) *Methods in Enzymol.* 112, 238–247.
35. Bennett, J., Maguire, A. M., Cideciyan, A. V., et al. (1999) *Proc. Natl. Acad. Sci. USA,* 96, 9920–9925.
36. Lau, D., McGee, L. H., Zhou, S., Rendahl, K. G., Manning, W. C., Escobedo, J. A., and Flannery, J. G. (2000) *Invest. Ophthalmol. Vis. Sci.,* 41, 3622–3633.
37. Stallwood, Y., Fisher, K. D., Gallimore, P. H., and Mautner, V. (2000) *Gene Therapy,* 7, 637–643.
38. Smith, J. G., Raper, S. E., Wheeldon, E. B., Hackney, D., Judy, K., Wilson, J. M., and Eck, S. L. (1997) *Human Gene Therapy,* 8, 943–954.
39. Dewey, R. A., Morrissey, G., Cowsill, C. M., et al. (1999) *Nature Medicine,* 5, 1256–1263.
40. McMenamin, M. M., Byrnes, A. P., Charlton, H. M., Coffin, R. S., Latchman, D. S., and Wood, M. J. A. (1998) *Neuroscience,* 83, 1225–1237.

41. Herrlinger, U., Kramm, C. M., Aboody-Guterman, K. S., et al. (1998) *Gene Therapy*, 5, 809–819.
42. Driesse, M. J., Vincent, A. J. P. E., Sillevis Smith, P. A. E., et al. (1998) *Gene Therapy*, 5, 1122–1129.
43. Byrnes, A. P., Rusby, J. E., Wood, M. J. A., and Charlton, H. M. (1995) *Neuroscience*, 66, 1015–1024.
44. Driesse, M. J., Esandi, M. C., Kros, J. M., et al. (2000) *Gene Therapy*, 7, 1401–1409.
45. Kramm, C. M., Rainov, N. G., Sena-Esteves, M., Chase, M., Pechan, P. A., Chiocca, E. A., and Breakefield, X. O. (1996) *Human Gene Therapy*, 7, 291–300.
46. Shastry, B. S. (2000) *IUBMB Life*, 49, 479–484.
47. Shi, N., Zhang, Y., Boado, R. J., Zhu, C., and Pardridge, W. M. (2001) *Proc. Natl. Acad. Sci. USA*, 98, 12754–12759.
48. Sugasawa, K., Deguchi, J., Okami, T., Yamamoto, A., Omori, K., Uyama, M., and Tashiro, Y. (1994) *Cell. Struct. Funct.*, 19, 21–28.
49. Baudouin, C., Brignole, F., Fredj-Reygrobellet, D., Negre, F., Bayle, J., Gastaud, P. (1992) *Invest. Ophthamol. Vis. Sci.*, 33, 2822–2829.
50. Yefimova, M. G., Jeanny, J., Guillonneau, X., Keller, N., Nguyen-Legros, J., Sergeant, C., Guillou, F., Courtois, Y. (2000) *Invest. Ophthalmol. Vis. Sci.*, 41, 2343–2351.
51. Brenner M., Kisseberth W. C., Su Y., Besnard F., Messing A. (1994) *J. Neurosci.* 14, 1030–1037.
52. Segovia J., Vergara P., Brenner M. (1998) *Neurosci Lett.* 242, 172–176.
53. Kissel K., Hamm S., Schulz M., Vecchi A., Garlanda C., Engelhardt B. (1998) *Histochem Cell Biol.* 110, 63–72.
54. MacKenzie D., Arendt A., Hargrave P., McDowell J. H., Molday R. S. (1984) *Biochem.* 23, 6544–6549.
55. Shi N., Pardridge W. M. (2000) *Proc Natl Acad Sci USA* 97, 7567–7572.
56. Miyoshi H., Takahashi M., Gage F. H., Verma I. M. (1997) *Proc Natl Acad Sci USA.* 94, 10319–10323.
57. Holash J. A., Stewart P. A. (1993) *Brain Res.* 629, 218–224.
58. Davis A. A., Hunt R. C. (1993) *J Cell Physiol.* 156, 280–285.
59. Yefimova M. G., Jeanny J. C., Guillonneau X., et al. (2000) *Invest Ophthalmol Vis Sci.* 41, 2343–2351.
60. Tan P. H., King W. J., Chen D., et al. (2001) *Transplantation.* 71, 552–560.
61. Zhuo L., Sun B., Zhang C. L., Fine A., Chiu S. Y., Messing A. (1997) *Dev Biol.* 187, 36–42.
62. Shi N., Boado R. J., Pardridge W. M. (2001) *Pharm Res.* 18, 1091–1095.
63. Naeser P. (1997) *Ups J Med Sci.* 102, 35–40.

What is claimed is:

1. A composition of matter for delivering a gene to an ocular cell, said composition of matter comprising:
    a liposome having an exterior surface and an internal compartment;
    a plurality of targeting agents comprising blood-retinal barrier and ocular cell membrane targeting agents to provide targeting of said liposome to an ocular cell;
    a plurality of conjugation agents wherein each targeting agent is connected to the exterior surface of said liposome via at least one of said conjugation agents; and
    a gene selected from the group consisting of opsin protein of rhodopsin gene, cyclic GMP phosophodiesterase α-subunit or β-subunit gene, the alpha subunit of the rod cyclic nucleotide gated channel gene, retinal pigmented epithelium-specific 65 kD protein gene, retinal binding protein 1 gene, ATP binding casette retina gene, peripherin/retinal degeneration slow gene, rod outer segment membrane protein 1 gene, arrestin gene, alpha-transducin gene, rhodopsin kinase gene, guanylate cyclase activator 1A gene, retina specific guanylate cyclase gene, the alpha subunit of the cone cyclic nucleotide gated cation channel gene and cone opsin genes, said gene being located within the internal compartment of said liposome.

2. A composition of matter according to claim 1 wherein said liposome exterior surface defines a sphere having a diameter of less than 200 nanometers.

3. A composition of matter according to claim 1 wherein said gene is located within a plasmid.

4. A composition of matter according to claim 1 wherein between 5 and 1000 targeting agents are conjugated to said exterior surface of said liposome.

5. A composition of matter according to claim 1 wherein between 25 and 40 targeting agents are conjugated to said surface of said liposome.

6. A composition of matter according to claim 1 wherein said conjugation agent is selected from the group consisting of polyethylene glycol, sphingomyelin and organic polymers.

7. A composition of matter according to claim 1 wherein said blood-retinal barrier targeting agent and ocular cell membrane targeting agent is the same targeting agent.

8. A composition of matter according to claim 1 wherein said targeting agent is selected from the group consisting of insulin, transferrin, insulin-like growth factor, leptin and low density lipoprotein.

9. A composition of matter according to claim 1 wherein said targeting agent is selected from the group consisting of peptidomimetic monoclonal antibodies that bind to the insulin-receptor on the blood-retinal barrier and peptidomimetic monoclonal antibodies that bind to the insulin receptor on the ocular cell membrane.

10. A composition of matter according to claim 1 wherein said targeting agent is selected from the group consisting of peptidomimetic monoclonal antibodies that bind to the transferrin receptor on the blood-retinal barrier and peptidomimetic monoclonal antibodies that bind to the transferrin receptor on the ocular cell membrane.

11. A composition of matter according to claim 1 wherein said targeting agent is selected from the group consisting of peptidomimetic monoclonal antibodies that bind to the insulin-like growth factor receptor on the blood-retinal barrier and peptidomimetic monoclonal antibodies that bind to the insulin-like growth factor receptor on the ocular cell membrane.

12. A composition of matter according to claim 1 wherein said targeting agent is selected from the group consisting of peptidomimetic monoclonal antibodies that bind to the leptin receptor on the blood-retinal barrier and peptidomimetic monoclonal antibodies that bind to the leptin receptor on the ocular cell membrane.

13. A composition of matter according to claim 1 wherein said targeting agent is selected from the group consisting of peptidomimetic monoclonal antibodies that bind to the low density lipoprotein receptor on the blood-retinal barrier and peptidomimetic monoclonal antibodies that bind to the low density lipoprotein receptor on the ocular cell membrane.

14. A composition of matter for delivering a gene to an ocular cell, said composition of matter comprising:
    a) a receptor-specific liposome comprising:
        a liposome having an exterior surface and an internal compartment;

a plurality of targeting agents comprising blood-retinal barrier and ocular cell membrane targeting agents to provide targeting of said liposome to an ocular cell;

a plurality of conjugation agents wherein each targeting agent is connected to said exterior surface of said liposome via at least one of said conjugation agents;

a gene selected from the group consisting of opsin protein of rhodopsin gene, cyclic GMP phosophodi-esterase α-subunit or β-subunit gene, the alpha subunit of the rod cyclic nucleotide gated channel gene, retinal pigmented epithelium-specific 65 kD protein gene, retinal binding protein 1 gene, ATP binding casette retina gene, peripherin/retinal degeneration slow gene, rod outer segment membrane protein 1 gene, arrestin gene, alpha-transducin gene, rhodopsin kinase gene, guanylate cyclase activator 1A gene, retina specific guanylate cyclase gene, the alpha subunit of the cone cyclic nucleotide gated cation channel gene and cone opsin genes, said gene being located within the internal compartment of said liposome;

b) a pharmaceutically acceptable carrier for said receptor-specific liposome.

15. A composition of matter according to claim 14 wherein said blood-retinal barrier targeting agent and said ocular cell membrane targeting agent is the same targeting agent.

* * * * *